US012741018B2

(12) United States Patent
Smith

(10) Patent No.: US 12,741,018 B2
(45) Date of Patent: Sep. 22, 2026

(54) VIRAL PANDEMIC VACCINE

(71) Applicant: Henry J Smith, Temecula, CA (US)

(72) Inventor: Henry J Smith, Temecula, CA (US)

( * ) Notice: Subject to any disclaimer, the term of this patent is extended or adjusted under 35 U.S.C. 154(b) by 93 days.

(21) Appl. No.: 17/194,308

(22) Filed: Mar. 7, 2021

(65) Prior Publication Data

US 2022/0280631 A1 Sep. 8, 2022

(51) Int. Cl.
*A61K 39/39* (2006.01)
*A61K 39/12* (2006.01)
*A61K 39/00* (2006.01)

(52) U.S. Cl.
CPC .... *A61K 39/12* (2013.01); *A61K 2039/55555* (2013.01)

(58) Field of Classification Search
None
See application file for complete search history.

(56) References Cited

U.S. PATENT DOCUMENTS 10,105,435 B2 * 10/2018 Mansour ................ A61P 37/08
2015/0328305 A1 * 11/2015 Smith .................... A61K 39/12 424/210.1

FOREIGN PATENT DOCUMENTS

WO WO2010/054654 * 5/2010 ............ A61K 9/127

OTHER PUBLICATIONS

Apostolico et al. (Frontiers in Immunology, 2019, p. 1-12).*

* cited by examiner

*Primary Examiner* — Agnieszka Boesen

(57) ABSTRACT

This invention teaches a means of rapidly producing a vaccine following a viral outbreak and using said vaccine to prevent the outbreak from becoming a pandemic. Said vaccine is composed of multiple immunostimulatory agents (agonists) incorporated in liposomes. Each agonist will bind to its specific cellular receptor and induce the cell to produce type 1 interferons which has strong anti-viral activity. The agonists are Poly IC, ssRNA, CpG-ODN and MPL-A incorporated in a liposomal vaccine. Using multiple different agonists in the vaccine will elicit a stronger innate immune response than using a single agonist. This vaccine can be enhanced by combining a viral antigen with the agonists in the liposome. Said enhanced vaccine will provide immediate and prolonged immunity to viral infection by stimulating both the innate immune response and the adaptive immune response against the virus.

2 Claims, No Drawings

VIRAL PANDEMIC VACCINE

CROSS-REFERENCE TO RELATED APPLICATIONS

This invention claims priority to provisional patent No. 63/101,302 titled "Vaccine to treat Viral Pandemics" filed Apr. 24, 2020, confirmation No. 3992; and to provisional patent No. 63/204,632 titled "Viral Pandemic Vaccine" filed Oct. 16, 2020, confirmation No. 2541.

FEDERALLY SPONSORED RESEARCH OR DEVELOPMENT

N/A.

BACKGROUND OF THE INVENTION

Vaccines have played a major role in global health. Many contagious diseases that in the past have killed or injured the health of millions of people worldwide have been controlled by government sponsored vaccination programs. This has resulted in the effective control of diseases such mumps, measles, and polio; and the eradication of smallpox.

However, we have witnessed viral pandemics that have killed millions of people worldwide. For example, the Spanish Flu in 1918-1920 which killed 50 million people; the Asian Flu in 1957-1958 which killed 2 million; and the Hong Kong Flu in 1968-1969 which killed about 1 million people.

In December 2019 a new strain of coronavirus-SARS-CoV-2 was identified as a cause of severe acute respiratory syndrome The disease caused by this coronavirus rapidly spread worldwide causing significant morbidity; and was designated as the COVID-19 pandemic by WHO. As of January 2021 there are over 400,000 deaths in the US and over 2,000,000 deaths worldwide. The number of deaths is expected to increase significantly before the COVID-19 pandemic is over.

The COVID-19 pandemic showed us that the world is totally unprepared to deal with pandemics caused by a new pathogenic strain of virus. There were no vaccines available to treat SARS-CoV-2, and the current antiviral drugs were found to be ineffective against the virus.

The reason why there are no vaccines to treat SARS-CoV-2 is obvious. Conventional wisdom teaches that it takes years to develop a safe and effective vaccine; by which time the pandemic caused by the new virus will have come and gone and caused hundreds of thousands of deaths in its wake. Even in this time of crisis with the ongoing COVID-19 pandemic, where a vast amount of scientific resources are being used to accelerate the development of a vaccine, most experts believe that it will take at least a year before a COVID-19 vaccine is developed and made available to the public.

Once a vaccine against SARS-CoV-2 is developed it can be used to vaccinate the general population from being infected with SARS-CoV-2; and when that happens most experts believe that the COVID-19 pandemic will be over and future outbreaks with SARS-CoV-2 can be contained.

But what happens if the next pandemic is not caused by SARS-CoV-2 but by a new pathogenic strain of coronavirus, or by a different new pathogenic virus. All the vaccines we have developed against COVID-19 and the other known pathogenic viruses will be rendered useless. We will be facing the same situation we had when the COVID-19 pandemic first started-. No vaccines to protect the population, and a rising death toll in the US and around the world. There appears to be very little research being done to address this fundamental problem—is it at all possible to develop a vaccine against an unknown pathogenic virus in time for it to be effective in preventing an initial viral outbreak from becoming a pandemic?

According to conventional wisdom the answer is "NO"—it is not possible to develop a vaccine in time to prevent a viral outbreak from becoming a pandemic. Because even with the most advanced technologies being used today it still takes many months and possibly years to develop a vaccine. And this is obviously not fast enough to prevent a viral outbreak from becoming a pandemic when the time to develop a vaccine is measured in days and weeks, and not months and years.

The novelty of this invention is that it teaches an unconventional approach to preparing a vaccine against an unidentified virus. It teaches a method of preparing this vaccine beforehand so that it can be immediately deployed to where it is needed within 24-48 hours of a viral outbreak by an unknown virus. Timely vaccination with this vaccine during the initial viral outbreak may prevent the viral infection from spreading and becoming a pandemic. Further, this protection is not limited to any particular virus but should also be effective against most if not all viruses.

This invention also teaches that this vaccine can be modified to enhance the immune response once the pathogenic virus has been identified. Timely vaccination with this enhanced vaccine during the initial viral outbreak may prevent the viral infection from spreading and becoming a pandemic. It can also be used to protect the population from a recurrence of the pandemic.

SUMMARY OF THE INVENTION

The novelty of this invention is that it teaches the best way to treat a viral pandemic caused by an unknown virus is to prevent the viral outbreak from spreading and becoming a pandemic. Conventional wisdom teaches that it typically takes years to develop a vaccine and therefore it is impossible to prepare a vaccine in time to treat the viral outbreak. This invention teaches an unconventional means of producing a vaccine immediately following a viral outbreak. Timely vaccination with this vaccine could prevent a viral outbreak from becoming a pandemic. The vaccine is composed of multiple immunostimulatory agents (agonists) incorporated in liposomes. The agonists will bind to cellular receptors and stimulate the innate immune response to produce type 1 interferons which have strong anti-viral activity. The agonists used in this vaccine are Poly IC, ssRNA, CpG-ODN and MPL-A. Using multiple different agonists in the vaccine will elicit a stronger innate immune response than using a single agonist. This vaccine can be enhanced by combining a viral antigen with the agonists in the liposome. Said enhanced vaccine will provide immediate and prolonged immunity to viral infection by stimulating both the innate immune response and the adaptive immune response. Optionally various adjuvants may be added to the vaccine to further enhance the immune response.

The vaccines disclosed in this invention are primarily designed to treat a viral outbreak and prevent it from becoming a pandemic. They can also be used to treat individuals who were exposed to viral infection during a pandemic or to protecting the general public from a recurrence of the pandemic.

This invention also teaches that a key element to the rapid development of a vaccine is to prepare and test beforehand wherever possible all the vaccine ingredients, and to then stockpile these ingredients until they are required. Once a viral outbreak caused by an unknown virus is identified the vaccine components that were stockpiled can be rapidly reconstituted and made into the finished vaccine.

DETAILED DESCRIPTION OF THE INVENTION

The ongoing COVID-19 pandemic has demonstrated how unprepared the world is in dealing with a viral outbreak caused by an unknown pathogenic strain of virus. The traditional methods of preparing a vaccine typically takes years when the time to respond to prevent a viral outbreak from becoming a pandemic is measured in days and weeks.

In order to treat a pandemic, time is of the essence. With pathogenic viruses the time from exposure to developing clinical symptoms is typically a matter of a few days, and then further progression from clinical symptoms to death may take only a few days more. This is because left unchecked the virus can multiply at a frightening speed within a susceptible or immunocomprised individual. In many instances the initial stage of viral infection presents with little outward signs and is often unrecognized or ignored. However, the infected individual may still shed infectious virus particles that can transmit the infection to others. And one infected individual can infect many others where conditions are crowded For example in shopping malls, sports stadiums, movie theaters, colleges and schools. And also in more local settings such as in restaurants, hair dressing salons, business meetings and at social events such as weddings and birthday parties. And with rapid transit systems such as the subway, planes, trains, and buses, the contagion can quickly spread far and wide before it is detected. This is because not only can the infected individual personally spread the infection to his or her destination; but other travelers who became infected during the trip will also spread the contagion to their destinations. In this context, it's important to remember that with the COVID-19 pandemic it only took a couple of months for the initial viral outbreak to spread and become a worldwide pandemic with catastrophic consequences.

There is a fundamental difference between conventional vaccines and the unconventional vaccine disclosed in this invention. Conventional vaccines typically take years to be developed and are designed to protect the general population from a recurrence of the pandemic. And as noted earlier conventional vaccines cannot protect the population from the initial viral pandemic. In contrast the vaccine of this invention is designed to prevent an initial viral outbreak caused by an unknown pathogenic virus from becoming a pandemic. This means that many of the conventional concepts and methods for preparing a vaccine cannot be employed. For example, traditional vaccines are designed to elicit a strong and durable adaptive immune response so that millions of individuals (i.e. most of the population) can be vaccinated and protected against an impending recurrence of a viral pandemic. Developing a vaccine to protect millions of people typically takes years. In contrast, the vaccine of this invention is designed to quickly protect a limited number of individuals that are exposed to the virus during the initial virus outbreak and thus prevent the infection from spreading and becoming a pandemic.

It is now widely recognized that there are two types of immune response: The "adaptive" (acquired) immune response and the "innate" immune response. Both types of immune response are involved in providing immunity to bacterial or viral infection. Traditional vaccines are designed to stimulate the adaptive immune response against viral antigens. The adaptive immune response takes time to develop and is characterized by the production of protective antibodies against the known pathogenic pandemic virus and the presence of immune cells (cytotoxic T lymphocytes) that will kill virus infected cells and thus limit the multiplication and spread of the virus. In contrast, the unconventional vaccine in this invention is designed to stimulate the innate immune response against viral infection by an unknown virus. In contrast to conventional vaccines the basic vaccine of this invention contains no viral antigens but only immunostimulatory compounds (agonists) that can stimulate cells to produce anti-viral compounds such as interferons and cytokines. The innate immune response is immediate and provides protection against all types of virus infection.

The innate immune response is the first line of defense against invading microorganisms such as bacteria and viruses. When cells are infected with a virus they produce an anti-viral compound that alerts other cells to defend themselves from being infected with the virus. This compound is called "interferon" (IFN). Most importantly, it was found that this protection was not limited to a single species of virus but would afford protection against all species of viruses.

Human interferons are classified into three major types: Interferon type I which includes IFN-α; IFN-β; IFN-ε; IFN-κ; and IFN-ω; Interferon type II which includes IFN-γ; and Interferon type III. In general when there is a virus infection the innate immune system responds by producing type I interferons which have potent anti-viral properties, and also cyokines that can upregulate IFN dependent genes in other cells to produce more anti-viral compounds.

The innate immune response is triggered by certain characteristic microbial molecular signatures binding to specific pattern-recognition receptors (PRR) present on the surface of a cell or within the endosome of the cell. These receptors are found in various cell types including natural killer cells, T and B lymphocytes, epithelial cells, fibroblasts, mononuclear cells, macrophages, and dendritic cells. In particular it was discovered that a subset of dendritic cells called plasmacytoid dendritic cells could be stimulated to produce extremely large amounts of type I interferon.

The microbial pattern recognition receptors are named "Toll-Like Receptors" (TLR) because of their similarity to the Toll receptor discovered in the fruit-fly *Drosophila*. There are 10 TLRs that have been identified to date in humans and each TLR is stimulated to respond to its own characteristic microbial pattern trigger. This invention teaches that there are certain TLRs that produce type I interferon in response to viral infection. These receptors are TLR3, TLR4, TLR7, and TLR9.

There are basically two groups of viruses: RNA viruses and DNA viruses. The innate immune system is preprogrammed to respond to viral RNA or viral DNA and produce type I interferons and various cytokines. However, it is important to note here that the innate immune system is also preprogrammed to respond to bacterial DNA and produce type I interferons; and that the interferons thus elicited will also protect against viral infection. The immunostimulatory agents used in the vaccine of this invention are agonists that bind to different TLRs and stimulate the production of type 1 interferons.

The synthetic agonist of double stranded viral RNA (dsRNA) that binds to TLR3 is polyinosinic:polycytidylic acid (Poly IC). Poly IC is a mismatched double-stranded RNA with one strand being a polymer of inosinic acid and the complementary strand being a polymer of cytidylic acid. It binds to TLR3 in the endosomes of cells and initiates the TIR-domain-containing adaptor-inducing interferon-β (TRIF) biochemical pathway leading to the production of type I interferons. In order to provide better stability in vivo a modified version of Poly IC was developed in which polyinosinic:polycytidylic acid is stabilized with poly-1-lysine and carboxymethylcellulose (Poly ICLC). Like poly IC, poly ICLC binds to TLR3 in the endosome and initiates the TRIF biochemical pathway leading to the production of type I interferons.

The agonist selected to bind to TLR4 is Monophosphoryl Lipid A (MPL-A) which is a detoxified endotoxin lipid A fraction extracted from the bacterium *Salmonella minnesota*. It is FDA approved and has been tested in clinical trials. There are also a number of synthetic MPL-A analogues that have been developed. TLR 4 is a transmembrane receptor; and when MPL-A binds to TLR4 it stimulates both the Myeloid differentiation primary response gene 88 (MyD88) and the TRIF biochemical pathways leading to the production of type 1 interferon and proinflammatory cytokines.

The synthetic agonist of single stranded viral RNA (ssRNA) is a synthesized single strand of RNA enriched with GU or poly-U sequences. The ssRNA binds to TRL 7 in the endosome and initiates the MyD88 pathway leading to the production of type I interferons. In one embodiment of this invention other TRL7 agonists such as resiquimod, imiquimod and gardiquimod may be used instead ssRNA in the vaccine to stimulate the production of interferon and cytokines.

The synthetic agonist of bacterial DNA that binds to TLR9 is a short single-stranded unmethylated CpG oligodeoxynucleotide that contain a cytosine triphosphate nucleotide "C" followed by a guanine triphosphate deoxynucleotide "G" linked by a phosphodiester or phosphorothioate backbone "p" (CpG-ODN). There are basically three classes of CpG-ODN: Class A CpG-ODN which is a strong inducer of type 1 interferon; Class B CpG-ODN which is weak at producing interferon but promotes survival, activation and maturation of plasmacytoid dendritic cells; and Class C CpG-ODN which combines certain features of Class A and Class B. In one embodiment of this invention Class A CpG-ODN is used to bind to TLR9 in th endosome and initiate MyD88 pathway leading to the production of type I interferons. In other embodiments of this invention Class B CpG-ODN or Class C CpG-ODN is used to bind to TLR9 in the endosome and initiate the MyD88 pathway leading to the production of type I interferons.

More recently another class of cytoplasmic pattern recognition receptors termed Retinoic Acid-Inducible Gene 1/Melanoma Differention-Associated protein 5 (RIG-1/MDAS) have been shown to respond to double-stranded viral RNA (dsRNA), or Poly IC and initiate the IFN-β promotor stimulator 1 (IPS-1) biochemical pathway leading to the production of type I interferon and proinflammatory cytokines.

This invention teaches that in order to maximize the innate immune response the liposomal vaccine is comprised of multiple different agonists with each targeting a different TLR receptor on a variety of different cells. These agonists include poly IC (or poly ICLC) which targets TLR3, MPL-A which targets TLR4, ssRNA which targets TLR 7, and CpG-ODN which targets TLR9.

The term "vaccine" is typically used to describe a procedure whereby an individual is administered a viral antigen, or a killed or attenuated viral preparation, in order to elicit an immune response that will protect the individual against a later infection with the live pathogenic virus. In this invention the term "vaccine" will be more generally used to include all preparations that are designed to elicit a protective immune response against a viral infection. It will include conventional vaccines that incorporate viral antigens in the vaccine; and will also include vaccines that do not incorporate viral antigens but only immunostimulatory compounds (agonists) to protect against viral infection.

In this invention the term "incorporated in a liposome" will include all the different ways in which the immunostimulatory agents are encapsulated, incorporated or attached to the liposome. For example, aqueous agents may be encapsulated within the aqueous interior of the liposome; lipid soluble agents may be incorporated in the lipid bilayer of the liposome, and some agents are attached to the lipid bilayer of the liposome through ionic charge binding.

In one embodiment of this invention the vaccine comprises a mixture of liposomal sub-unit vaccines with each incorporating a different immunostimulatory agent (agonist) i.e. a liposomal poly IC (or poly ICLC) sub-unit vaccine; a liposomal ssRNA sub-unit vaccine; a liposomal CpG-ODN sub-unit vaccine; and a liposomal MPL-A subunit-vaccine. These liposomal sub-unit vaccines are then mixed together to prepare the complete vaccine. In one embodiment of this invention the sub-unit vaccine may comprise several agonists e.g. poly IC and ssRNA; or poly IC and CpG-ODN; or CpG-ODN and MPL-A etc.

In one embodiment of this invention all the agonists are incorporated into the liposome. The ratio (w/w) of the agonists combined in the vaccine are initially: 1 poly IC: 1 ssRNA: 1 CpG-ODN: 0.1 MPL-A. These initial values were selected based on the reports of various clinical studies that examined their individual safety and efficacy profiles for treating different diseases. However, the final amounts of each agonist to be used in the final FDA approved vaccine will ultimately depend upon the results obtained from testing the vaccine in animals and in clinical trials in humans.

The following examples will illustrate the teaching in this invention regarding the preparation of these vaccines. They are provided for illustration only and are not to be construed as a limitation on the composition of the liposome or how such vaccines can be prepared. One of ordinary skill in the art would be aware of the many modifications that can be made to the methods taught in this invention without departing from the spirit and scope of this invention.

In this invention the liposomes are prepared using one or more phospholipids selected from the following list: phosphatidylcholine (PC), egg phosphatidylcholine (EPC), hydrogenated egg phosphatidylcholine (HEPC); soy phosphatidylcholine (SPC), hydrogenated soy phosphatidylcholine (HSPC), phosphatidylethanolamine (PE), phosphatidylglycerol (PG), phosphatidylinositol (PI), monosialoganglioside and sphingomyelin (SPM); distearoylphosphatidylcholine (DSPC), dimyristoylphosphatidylcholine (DMPC), dimyristoylphosphatidylglycerol (DMPG), dipalmitoylphosphatidylcholine (DPPC), dioleoylglycerophosphocholine (DOPC); dioleoylphosphatidylethanolamine (DOPE); and distearoylphosphatidylethanolamine (DSPE-PEGn) where n is a polymer with a MW equal or greater than 2,000 daltons. Cholesterol is typically included in the formulation.

In one embodiment of this invention cationic liposomes are used to prepare the vaccine. To prepare the cationic liposomes one or more cationic lipids is selected from the following list: dimethyldioctadecyl-ammonium bromide (DDAB); 1,2-dioleoyl-3-trimethylammonium-propane (DOTAP); 1,2-dioleyloxy-3-dimethylaminopropane (DODMA); 1,2-dimyristoyl-3-trimethylammonium-propane (DMTAP), 1,2-di-O-octadecenyl-3-trimethylammonium propane (DOTMA); 1,2-distearoyl-sn-glycero-3-ethylphosphocholine (EPC); 3β-[N-(1,2-dimyristoyl-3-trimethylammonium-propane (DMTAP), and N',N'-dimethylaminoethane)-carbamoyl-cholesterol hydrochloride (DC-Chol);

In one embodiment of this invention the vaccine comprises a mixture of several sub-unit vaccines composed of cationic liposomes each incorporating a different immunostimulatory agent. For example, one sub-unit vaccine comprises poly IC incorporated in a cationic liposome, another sub-unit vaccine comprises ssRNA in a cationic liposome; another sub-unit vaccine comprises CpG-ODN incorporated in a cationic liposome, and yet another sub-unit vaccine comprises MPL-A incorporated in a cationic liposome. The individual sub-unit vaccines are then mixed together to form the final vaccine. The use of sub-unit vaccines is particularly useful in initial studies to determine the appropriate concentration of each individual agonist to be used in the final combined vaccine.

The following examples will illustrate the preparation of a sub-unit vaccine in which each of the immunostimulatory agents (agonists) are incorporated individually in a cationic liposome.

Example 1. Preparation of a Sub-Unit Vaccine Comprising Poly IC in a Cationic Liposome Cationic liposomes were prepared by the thin film hydration method. DOPE, MC-Cholesterol and DSPE-PEG2000 were dissolved in chloroform/methanol solutions and mixed at the desired molar ratios: 55 DOPE; 45 MC-Cholesterol; 0.05 DSPE-PEG2000. The organic solvent was evaporated by rotary evaporation under vacuum to obtain a lipid film. The lipid film is hydrated with a solution of poly IC dissolved in distilled water. The ratio of poly IC:lipid used is 1:10. The hydrated lipid solution is sonicated in a water-bath sonicator until a clear to translucent solution is obtained. This indicates the formation of small liposomes in which the poly IC is encapsulated and/or bound to the liposome membrane through electrostatic charge effect. The liposomes are frozen and then freeze-dried. The lyophilized poly IC liposomes are stored under nitrogen gas in a sealed vial at −20 C.

Example 2. Preparation of a Sub-Unit Vaccine Comprising ssRNA in a Cationic Liposome This method is essentially the same as that disclosed in Example 1 except that ssRNA is used instead of Poly IC. The liposomes are frozen and then freeze-dried. The lyophilized ssRNA liposomes are stored under nitrogen gas in a sealed vial at −20 C.

Example 3. Preparation of a Sub-Unit Vaccine Comprising CpG-ODN in a Cationic Liposome This method is essentially the same as that disclosed in Example 1 except that CpG-ODN is used instead of Poly IC. The liposomes are frozen and then freeze-dried. The lyophilized CpG-ODN liposomes are stored under nitrogen gas in a sealed vial at −20 C.

Example 4. Preparation of a Sub-Unit Vaccine Comprising MPL-A in a Cationic Liposome This method is essentially the same as that disclosed in Example 1 except that MPL-A is used instead of Poly IC. Also the MPL-A is lipid soluble and is combined with the lipids used to prepare the liposomes. The ratio of MPL-A to total lipids is 1:10. The liposomes are prepared by the same process as described in Example 1. The MPL-A being lipid soluble is incorporated into the lipid bilayer membrane of the liposome. The liposomes are frozen and then freeze-dried. The lyophilized MPL-A liposomes are stored under nitrogen gas in a sealed vial at −20 C.

To prepare the complete vaccine the freeze-dried sub-unit vaccines are mixed together in the following amounts (w/w): 1 poly IC liposomes: 1 ssRNA liposomes: 1 CpG-ODN liposomes: 0.1 MPL-A liposomes. Depending on the results of animal and human clinical studies these amounts may be modified. The mixed freeze-dried liposomes are then stored under nitrogen gas in a sealed vial at −20 C. To prepare the vaccine for administration the freeze-dried mixed liposomes are rehydrated using distilled water, and the vaccine vial is sonicated in a water-bath sonicator until the liposome suspension becomes translucent indicating the formation of small liposomes suitable for administration.

The vaccine may be administered by intramuscular, intradermal, or subcutaneous injection. It may also be administered intranasally which may be the preferred method for protecting against respiratory virus infection. In one embodiment of this invention in order to obtain the maximum immune response as rapidly as possible the vaccine is administered into multiple discrete sites in the individual. For example, intramuscular injections into the left and the right arm of the individual; or an intramuscular injection accompanied with intranasal administration.

In one embodiment of this invention the liposomal vaccine comprises multiple agonists incorporated together within a liposome. Said agonists are: poly IC; ssRNA; CpG-ODN; and MPL-A

Example 5. Preparation of a Vaccine Comprising Poly IC, ssRNA, CpG-ODN and MPL-A in a Cationic Liposome Cationic liposomes were prepared by the thin film hydration method. DOPE, MC-Cholesterol and DSPE-PEG2000 were dissolved in chloroform/methanol solutions and mixed at the desired molar ratios: 55 DOPE; 45 MC-Cholesterol; and 0.05 DSPE-PEG2000. To this was added an amount of MPL-A that was 1:250 (w/w) of total lipid. The organic solvent was evaporated by rotary evaporation under vacuum to obtain a lipid film. The lipid film was hydrated with a solution of poly IC, ssRNA, and CpG-ODN dissolved in distilled water. The ratio of poly IC:lipid used is 1:25, the ratio of ssRNA:lipid used is 1:25, and the CpG-ODN:lipid used is also 1:25 Depending on the results of clinical studies these amounts may be modified. The hydrated lipid solution was sonicated in a water-bath sonicator until a translucent solution was obtained. This indicated the formation of small liposomes. The liposomes are frozen and then freeze-dried. The lyophilized liposomes are stored under nitrogen gas in a sealed vial at −20 C. To prepare the vaccine for administration the freeze-dried liposomes are rehydrated using distilled water. The vaccine vial is then sonicated in a water-bath sonicator until the liposome suspension becomes translucent indicating the formation of small liposomes suitable for administration.

The vaccine may be administered by intramuscular, intradermal, or subcutaneous injection. It may also be administered intranasally which may be the preferred method for protecting against respiratory virus infection. In one embodiment of this invention in order to obtain the maximum immune response as rapidly as possible the vaccine is administered into multiple discrete sites in the individual. For example, intramuscular injections into the left and the right arm of the individual; or an intramuscular injection accompanied with intranasal administration.

To facilitate the rapid preparation and deployment of this vaccine to where it is needed the following steps can be instituted beforehand. For example, the bulk manufacture of the liposomes incorporating the immunostimulatory agents can be done at a central vaccine manufacturing facility under cGMP guidelines. There are many methods of producing liposomes on a commercial scale. These include the traditional methods of lipid film hydration, sonication, extrusion and reverse phase evaporation; and more, recent techniques like the microfluidization, microencapsulation, ethanol injection, freon injection and detergent dialysis methods.

The bulk vaccine in dispensed into sterile vials and lyophilized. Some of the vaccine vials are reconstituted with distilled water and tested for sterility and to conform to QA standards. They are then tested for safety and efficacy in animal studies and human clinical trials. Following FDA approval the lyophilized vaccines are then distributed to strategically located medical centers in different cities. They are stored on-site at −20 C until they are needed. Each medical facility will be required to have a bath sonicator and certain accessories such as syringes for vaccination and/or devices for intranasal administration. To reconstitute the lyophilized vaccine sterile distilled water is added to the vial which is shaken and then sonicated in a water-bath sonicator to produce the liposomal vaccine. The vaccine is then dispensed into the individual doses required for vaccination.

This vaccine is designed to stimulate the innate immune response prior to the individual becoming infected and exhibiting signs of clinical infection. First responders, and those exposed to viral infection but have not developed clinical signs of infection are candidates to receive the vaccine. This vaccine is not recommended to be used in individuals who present with clinical signs of viral infection because for these individuals it is probably too late for the vaccine to be effective, and there is also the risk of precipitating a "cytokine storm".

This invention further teaches that once the pathogenic virus causing the viral outbreak is identified it is possible to prepare an enhanced version of the vaccine by incorporating viral antigens in the vaccine. Said vaccine is designed to stimulate both the innate immune system and the adaptive immune system. There are two different types of viral antigen that can be employed: 1) A viral antigen prepared from a known strain of the virus that cross-reacts with the new pathogenic virus and 2) a viral antigen prepared from the new pathogenic strain. A vaccine that incorporates a cross-reacting viral antigen can be developed within a few weeks of the viral outbreak, whereas a vaccine that incorporates a viral antigen prepared from the pathogenic virus will take many months to prepare. In both cases there are several procedure that need to be instituted beforehand in order to accelerate their development. For example, 1) There must be a rapid standardized method of identifying the new virus; 2) There must be a stockpile of viral antigens prepared from various known strains of pathogenic viruses; 3) There must be a variety of cell cultures available to allow maximum growth rate of the new pathogenic virus; 4) There must be a serological test panel composed of human sera that have antibodies to known pathogenic viruses; 5) There must be a stockpile of the vaccine incorporating immunostimulatory agents and 6) There must be a stockpile of materials and accessories required to prepare and administer the vaccine such as disposable syringes and disposable intranasal delivery devices.

The following examples are provided for illustrative purposes only to demonstrate how the vaccines disclosed in this invention can be developed and used to prevent a viral outbreak from becoming a pandemic and/or to prevent an epidemic from becoming a pandemic, and/or to treat an ongoing pandemic and/or to protect against a recurrence of the pandemic. We will use a hypothetical pandemic scenario caused by a hypothetical novel coronavirus which we can designate as "SARS-X" to illustrate in practical terms the teachings in this invention. It will be obvious that the same teaching can be applied to other pathogenic viruses capable of causing a pandemic.

Example 6. Preparation of a liposomal vaccine comprising multiple immunostimulatory agents and a cross-reacting viral antigen within a liposome. In this hypothetical scenario a viral outbreak has occurred with significant morbidity and genomic analysis has identified it as a novel coronavirus which we will call "SARS-X". The SARS-X virus is immediately grown in various cell cultures that will support rapid growth of the virus. This is done at a vaccine manufacturing facility. Tissue or fluid samples from patients and/or from infected cell-cultures are also immediately tested for cross-reactivity to known strains of coronavirus using a coronavirus serological test panel. This panel consists of individual sera obtained from individuals who have recovered from an infection with a particular strain of coronavirus and have antibodies to that strain. For example, a panel of sera containing antibodies to known coronavirus strains (i.e. anti-SARS-Cov-2 antibody, anti-SARS-CoV antibody, and anti-MERS-CoV antibody). Each antibody is tested for binding activity to tissue and fluid samples obtained from an individual infected with the virus, or to viral cell culture fluid. A typical immunological test for binding activity in tissues is the indirect immunofluorescent assay (IFA) which takes about a day to perform. There are also other tests such as the enzymelinked-immunosorbent assay (ELISA) that can be used to test fluid samples and also take about a day to perform. These tests can be done at a vaccine manufacturing facility or by a viral testing laboratory. In this example for purposes of illustration assume that the anti-MERS-CoV antibody showed the best binding to the sample while the other anti-coronavirus antibodies showed less or no binding activity. This would indicate that the MERS-CoV virus shared common antigens with SARS-X virus and therefore the stockpiled MERS-CoV viral antigen could be used to prepare a vaccine that would elicit cross-reactive immunity against SARS-X.

Preparation of the virus incorporated vaccine can be done very rapidly at a vaccine manufacturing facility. The MERS-CoV antigen that has been stockpiled is diluted with distilled water or buffer to the desired concentration for administration. The stockpiled viral antigen could be in the form of killed viral particles; or a purified viral antigen; or a recombinant viral antigen. The lyophilized vaccine incorporating immunostimulatory agents that was disclosed in Example 5 is then reconstituted with the diluted MERS-CoV antigen solution, and shaken and sonicated to prepare the finished vaccine using the same process as described in Example 5. The finished vaccine is dispensed into individual vaccination doses and administered intranasally and/or by intramuscular, or intradermal or subcutaneous injection.

The cross-reactive antigen and immunostimulatory vaccine disclosed in Example 6 can be prepared very quickly after the viral outbreak. It takes about a day or two to identify the virus; another day or two to perform serological testing; and another day or two to prepare the final vaccine. Under the best circumstances the vaccine can be prepared within a week or two after the initial viral outbreak. No other vaccine under development comes close to this time-frame. However, this can only be accomplished when the appropriate procedures are implemented beforehand.

The cross-reacting viral antigen vaccine disclosed in Example 6 is primarily an interim measure to contain the outbreak until a vaccine incorporating the antigens from the pathogenic virus is developed. Again, using the hypothetical SARS-X virus as an example we can teach how this can be done in as short a time as possible. As noted earlier once a viral outbreak caused by a pathogenic virus occurs it takes about a day or two to identify the virus as a new strain of coronavirus which we have called SARS-X. The virus is immediately grown in cell culture under conditions designed to stimulate viral multiplication. Typically the virus multiplies very rapidly in culture and after several weeks there will be sufficient virus grown to prepare a limited amount of virus to be used to prepare a vaccine. Note, in contrast to traditional vaccines where a very large amount of viral antigen is required to vaccinate hundreds of millions of people to protect them from a recurrence of the pandemic, this invention teaches preparing a very small amount of viral antigen required to vaccinate a few hundred or a few thousand individuals that are likely to be exposed to an ongoing viral outbreak.

Example 7. Preparation of a Liposomal Vaccine Incorporating Multiple Immunostimulatory Agents and a Killed Preparation of the Pandemic Virus within a Liposome Preparation of this vaccine is relatively quick and straightforward and is done at a vaccine manufacturing facility. First the SARS-X virus is grown in cell culture until it reaches a suitable density to make a viral preparation for the vaccine. In this invention in order to save time a preparation of whole viral particles is used. To ensure there are no infectious particles in the preparation the virus is killed using heat treatment or chemicals that are then removed from the viral preparation. In one embodiment of this invention the virus is killed using beta-propiolactone which hydrolyses to an innocuous substance within a few hours after treatment. A purified preparation of killed viral particles is then prepared using known method of viral purification such as filtration and sedimentation. The purified killed SARS-X virus particles are then suspended in sterile distilled water or buffer to a concentration suitable for administration and used to reconstitute the lyophilized immunostimulatory vaccine described in Example 5. The mixture is shaken and sonicated to prepare the finished enhanced vaccine. In this vaccine because of the size of the virus particles in relation to the size of the liposomes many of the viral particles will not be encapsulated within the liposome. However, the viral particles will be in close proximity to the liposomes and to the immunostimulatory agents incorporated in the liposomes, and this close proximity will stimulate the immune response to the virus.

Another benefit of using a preparation of whole virus particles is that it contains the viral genome and this may have an added effect of stimulating the innate immune response against the virus.

In one embodiment of this invention one or more FDA approved adjuvants are added to the vaccine. Said adjuvants include alum, incomplete Freund's adjuvant, MF59 and other known adjuvants approved for clinical use. Adding one or more FDA approved adjuvants to the vaccine will boost the adaptive immune response to the viral antigen. With certain adjuvants such as alum the vaccine is simply mixed with the alum to prepare the final vaccine. With other adjuvants such as the oil based adjuvants the vaccine is mixed with the adjuvant and the mixture is blended to form an emulsion. Under the best circumstances it will be possible to prepare this vaccine within a few months of the viral outbreak. However, additional time will be required to test its safety and efficacy in animals and in non-human primates, and then in human trials before it can be released to treat the general population.

Although the vaccines in this invention are primarily designed to treat a viral outbreak to prevent it from becoming a pandemic they can also be used to protect individuals during an ongoing pandemic. For example, consider the current COVID-19 pandemic that has been going on for over a year and is likely to continue for some time. During this period there are intensive efforts being made to develop a vaccine to treat COVID-19 and hopefully one or more of these vaccines will be effective in controlling the pandemic. There is however, one important concern that must be addressed. The individuals vaccinated with the COVID-19 vaccine in the initial studies were all healthy individuals and therefore most likely to develop a protective immune response when later exposed to infection. There is however, very little data on the effectiveness of the vaccine in protecting individuals who are recently exposed to viral infection i.e. first responders, healthcare workers and those in recent contact with infected individuals. There is the distinct possibility that these vaccines will be less effective in these situations. This is because the current vaccines being developed are designed to stimulate the adaptive immune response which could take a week or more to develop, which may be too late to be effective in protecting individuals already exposed to infection. Further there is also the risk that stimulating the adaptive immune response in an individual who is recently infected or exposed to infection may precipitate a "cytokine storm" because it could exacerbate the patient's own immune response to the infection. The reason for this is that the adaptive immune response elicited by these vaccines would kick-in about the same time that the infected individual would be developing their own immune response to an ongoing viral infection, and it may be a case of "adding fuel to the fire". More research is needed to investigate this potential problem.

A vaccine that is designed to stimulate the innate immune response may be a better option for those individuals who may be recently exposed to viral infection. The reason is that this innate immunity is elicited almost immediately following vaccination and before the virus has the opportunity to multiply and establish itself. In this context it is important to note that the capacity of the virus to multiply exponentially imposes a very limited period of time after exposure to administer the vaccine for it to be effective. Also many viruses are known to have mechanisms for evading or inhibiting the immune response once they infect the cell, and therefore early vaccination could prevent the viruses for employing these defenses against the innate immune response of the host. Examples of individuals who would need immediate vaccination because they were recently exposed to viral infection include: first responders, healthcare workers and individuals exposed to the virus and those identified through contact tracing. During an ongoing pandemic these individuals would be the ones most likely to benefit from being vaccinated with a vaccine designed to stimulate the innate immune response as taught in this invention.

Many of the current vaccines being developed by vaccine manufacturers appear to be weakly immunogenic and require a booster dose several weeks after the initial dose in order to develop protective antibodies as an indication that the vaccination was successful. Typically, the composition of the vaccine administered in the booster dose is the same as that given in the initial vaccine. In one embodiment of this invention a similar vaccination schedule is applied in order to achieve an optimum immune response; but with a difference. In this invention the initial vaccine is composed of agonists and viral antigen designed to immediately stimulate the innate immune response followed by the adaptive immune response. It will not incorporate any adjuvants as this may delay the exposure of the vaccine components to antigen processing cells. However. the booster vaccine administered 1-4 weeks later will incorporate one or more adjuvants added to the vaccine. This combination of first stimulating the innate immune response followed by stimulating the adaptive immune response may be more effective than only stimulating the adaptive immune response.

The enhanced vaccines disclosed in this invention that incorporate a mixture of agonists and a viral antigen may also be a better choice to treat a pandemic than vaccines that are only designed to stimulate the adaptive immune response. This is because a vaccine that stimulates both the innate and adaptive immune response can provide both immediate and extended protection against infection. This feature may be particularly important in treating pandemics where the virus has a high rate of infection and can spread rapidly through the population.

All the experts agree that vaccines represent the best approach to treating a pandemic, but few then go on to qualify that statement by explaining that these vaccines are only effective at treating the late stages of an ongoing pandemic or a recurrence of the pandemic, but not the original pandemic when it first occurred. And this is what happened with the COVID-19 pandemic. Many people were surprised to find that there were no vaccines to treat COVID-19 and that it would take many months if not years before a vaccine was developed. This situation is not unique to COVID-19 but applies to all pandemics that are caused by a previously unknown pathogenic virus. It happened with previous pandemics; it happened with COVID-19; and it will happen again with future pandemics if the problem is not addressed.

This invention attempts to address this problem by teaching a rapid method of developing a vaccine in order to prevent a viral outbreak from becoming a pandemic. It teaches a vaccine that is designed to stimulate the innate immune response. It also teaches how this basic vaccine can be modified to stimulate both the innate immune response and the adaptive immune response. In this invention the term "vaccine" is used in the broadest sense to include a conventional vaccine preparation that includes viral antigens, as well as an unconventional vaccine that has no viral antigens but only immunostimulatory agents.

There is one important issue that must be addressed when a vaccine to a pandemic virus is developed in this manner. How can we be sure that this vaccine is safe and effective before we can use it. There is no easy answer. Obviously we cannot vaccinate millions of people with a vaccine that has not been extensively tested for safety and efficacy. But this can take many months and during this time people will be dying because there is no vaccine available to treat this new pandemic. There must be a way to solve this dilemma.

We can start by considering the vaccine composed of only immunostimulatory agents incorporated in liposomes. There is extensive research demonstrating that these immunostimulatory agents are already being used as adjuvants to enhance the immune response to various infectious agents and to cancer. Therefore it is very likely that combining these agents in a vaccine would be safe and not elicit serious side-effects. The vaccine will be tested beforehand using animal studies and human trials to confirm safety and to find the correct dose to use against a variety of different viruses. This is done as soon as possible and prior to a future pandemic. Therefore when the next viral outbreak caused by an unknown virus occurs the vaccine is already established to be safe to administer. Also the vaccine is intended to be administered to a limited number of individuals who have a high risk of being exposed to the pathogenic virus (e.g. first responders, healthcare workers, and those exposed to the virus and their contacts).

The situation is somewhat different for a vaccine that incorporates a recombinant viral antigen or killed viral particles combined with the immunostimulatory agents. Prior testing of the immunostimulatory agents vaccine will have established that it is safe, and it could be assumed that adding a non-infectious viral antigen or non-infectious viral preparation to the vaccine would not make it unsafe. However, to be extra careful it will have been tested beforehand for safety and efficacy in animals and limited trials in non-human primates prior to it being released. Also this vaccine is intended to be administered to a limited number of individuals who have a high risk of being exposed to the pathogenic virus (e.g. first responders, healthcare workers, and those exposed to the virus and their contacts).

The situation is completely different when we are considering vaccinating millions of people during an ongoing pandemic, or to protect them from a recurrence of the pandemic. Even though the vaccines are made to be non-infectious there has to be maximum testing and consideration given to ensure that they are safe and effective. There will need to be animal studies and testing in non-human primates. This will be followed by clinical trials in humans starting with a limited number of individuals and then by large scale testing involving thousands of individuals. And even with the accelerated testing guidelines being implemented by FDA today it will still take many months to complete the process. This delay is unavoidable unless a better accelerated testing protocol can be devised. However, it's important to note that once these vaccines are proven to be safe and effective they could be used to treat an ongoing pandemic, or a later recurrence of a pandemic caused by the same pathogenic virus.

Vaccines represent the best approach to treating a pandemic but they should be viewed in the broader context of how they can be used in conjunction with all the other steps taken to control a pandemic. For example, a vaccine to prevent an initial outbreak from becoming a pandemic will only be optimally effective if used in conjunction with public health measures such as immediate quarantine of the viral outbreak area in order to prevent the infection from spreading to other areas.

Also the immune response will obviously be most effective in preventing infection with a low dose of the virus than from a higher dose of the virus. Therefore public health measures such as social distancing and wearing masks are important measures to ensure that if infection occurs it will be at a low viral dose and will not result in a serious illness or death.

Another example is that viral pandemics don't recognize boundaries between States, or borders between countries. Therefore vaccination programs must be addressed both on the national level as well as on a global level. This is to ensure that information and resources can be shared and deployed most effectively to where they are most needed.

The effort to control pandemics must be at the governmental level. Vaccine manufacturers are not in the business of making, testing and stockpiling viral antigens and vaccine components that may never be used. And they are not in the business of doing basic research where the outcome is uncertain or not likely to be profitable. All the more reason why unconventional approaches to address seemingly intractable problems should be encouraged and supported by the government.

This invention discloses a means of rapidly preparing a vaccine to prevent a viral outbreak from becoming a pandemic. This invention uses a hypothetical unknown coronavirus in a pandemic scenario to illustrate the teaching of this invention in practical terms. It will be obvious to those of skill in the art that the same principles can be applied to prevent or treat other pandemics caused by an unknown virus or a new virulent strain of a known virus e.g. pathogenic strains of influenza A or a new virulent strain of coronavirus. In this context it is concerning to note that SARS-CoV-2 is mutating with some variants becoming more contagious and also possibly more virulent. Also, that the current vaccines being developed against SARS-CoV-2 may be less effective against some of the new SARS-CoV-2 variants.

Another area of concern is that the coronaviruses causing human infection may have arisen from bat coronaviruses; and if it happened in the past it could happen again. Also the fact that some coronaviruses can jump from one species to another could result in the appearance of more virulent strains to infect humans.

There is an urgent need to develop new approaches to developing vaccines that can be deployed in a timely manner to treat pandemics. This invention teaches one such approach. Those of skill in the art will be aware that there are many variations and modification to this teaching that can be made without departing form the spirit and scope of this invention. Said modifications and changes are therefore considered to lie within the scope of this invention.

This invention teaches a means of rapidly developing a vaccine to treat a viral outbreak caused by a previously unknown pathogenic virus in order to prevent it from spreading and becoming a pandemic. It also teaches several enhanced versions of the vaccine which can be used to treat an ongoing viral pandemic or a recurrence of the pandemic. The vaccines disclosed in this invention can be tested for safety and efficacy in animal models and human trials using known viruses; but we will not know for sure how they will work against a new pathogenic virus with the potential to cause a pandemic until it actually happens. However, despite this uncertainty regarding its effectiveness against an unknown virus this is still an approach that deserves further study. Because until researchers come up with a better solution all methods of developing vaccines for the next viral pandemic must be investigated.

What is claimed is:

1. A method of preventing a viral outbreak caused by an unidentified virus from becoming a pandemic by vaccinating individuals at risk of infection with a liposomal vaccine composed solely of four immunostimulatory agents incorporated in a liposome; and wherein said immunostimulatory agents are poly IC or poly ICLC, ssRNA, CpG-ODN, and MPL-A.

2. A method of preventing a viral outbreak caused by an unidentified virus from becoming a pandemic according to claim 1 by administering the vaccine by intranasal administration or by intramuscular or intradermal or subcutaneous injection.

* * * * *